United States Patent [19]
Oefner et al.

[11] Patent Number: 5,846,832
[45] Date of Patent: Dec. 8, 1998

[54] APPARATUS AND METHOD FOR SHEAR BREAKAGE OF POLYNUCLEOTIDES

[75] Inventors: Peter Josef Oefner, Innsbruck, Austria; Scott P. Hunicke-Smith, Menlo Park, Calif.

[73] Assignee: The Board of Trustees of the Leland Stanford Junior University, Stanford, Calif.

[21] Appl. No.: 717,278

[22] Filed: Sep. 20, 1996

Related U.S. Application Data

[60] Provisional application No. 60/004,040 Sep. 20, 1995.
[51] Int. Cl.[6] .............................. G01N 33/00; C12M 3/04; B01D 11/02; C12N 15/02
[52] U.S. Cl. ........................... 436/94; 536/23.1; 536/25.4; 435/285.1; 435/286.5; 435/286.6; 422/50; 422/63; 422/243; 422/281; 422/295; 935/76; 935/85
[58] Field of Search ................................... 436/94; 435/6, 435/91.1, 285.1, 286.5, 286.6; 422/50, 63, 243, 281, 295; 935/76, 85

[56] References Cited

U.S. PATENT DOCUMENTS 5,506,100   4/1996   Surzycki et al. ............................ 435/6

OTHER PUBLICATIONS

Reese et al., "Fractur of polynucleotide chains in extensional flow: Experiments with DNA, and a molecular–dynamics simulation," J. Chem. Phys. vol. 92, No. 4, pp. 2650–2662, Feb. 15, 1990.

M. A. MacConaill, "Biophysics Sedimentation of Deoxyribonucleic Acid isolated under Low Hyrodynamic Shear," Nature, vol. 185, pp. 918–920, Mar. 26 1960.

Bowman et al., "Hydrodynamic Shear Breakage of DNA," Biopolymers, vol. 11, pp. 2601–2624, 1972.

Bowman, R.D., and Davidson, N., "Hydrodynamic Shear Breakage of DNA," *Biopolym.* 11:2601–1624 (1972).

Cavalieri, L.F., and Rosenberg, B.H., "Shear Degradation of Deoxyribonucleic Acid," *J. Amer. Chem. Soc.* 81:5136–5139 (1959).

Davison, P., "The Effect of Hydrodynamic Shear on the Deoxyribonucleic Acid from $T_2$ and $T_4$ Bacteriophages," *Proc. Natl. Acad. Sci.* 45:1560–1568 (1959).

Davison, P., "Sedimentation of Deoxyribonucleic Acid Isolated Under Low Hydrodrnamic Shear," *Nature* 185: 918–920 (1960).

Larson, R.G., "The Unraveling of a Polymer Chain in a Strong Extensional Flow," *Rheol. Acta* 29:371–384 (1990).

Reese, H.R., and Zimm, B.H., "Fracture of Polymer Chains in Extensional Flow: Experiments with DNA and a Molecular–Dynamics Simulation," *J. Chem. Phys.* 92(4): 2650 (1990).

Rosenkranz, H.S., and Bendich, A., "Physicochemical Effects of High–Speed Mixing on Deoxyribonucleic Acid," *J. Amer. Chem. Soc.* 82:3198–3201 (1960).

Frenkel, J., "Orientatino and Rupture of Linear Macromolecules in Dilute Solutions under the Influence of Viscous Flow," *Acta Physiochim. URSS* 19:51–76 (1944).

*Primary Examiner*—Bradley L. Sisson
*Attorney, Agent, or Firm*—Charles K. Sholtz; Peter J. Dehlinger

[57] ABSTRACT

Apparatus and method for producing a defined size distribution of polynucleotide fragments having a selected mean size range between about 100 and 20,000 base pairs. The method includes passing a suspension of polynucleotide fragments through an apparatus containing a capillary with an orifice near the outlet end of the capillary.

26 Claims, 13 Drawing Sheets

APPARATUS AND METHOD FOR SHEAR BREAKAGE OF POLYNUCLEOTIDES

This invention was made with Government support under grant 1P01-HG00205-05 awarded by the National Institutes of Health. Accordingly, the United States Government has certain rights in this invention.

This application claims priority to Provisional U.S. patent application Ser. No. 60/004,040, filed 20 Sep. 1995, herein incorporated by reference.

FIELD OF THE INVENTION

The present invention relates to an apparatus and method for generating a defined distribution of DNA fragments. In particular, the invention relates to an apparatus and method for generating a distribution of DNA fragments with a selected mean between about 100 and 20,000 bp, and about a 2-fold size distribution.

REFERENCES

Anderson, S., *Nucl. Acids Res.* 9:3015–3027 (1981).
Ausubel, F. M., et al., *CURRENT PROTOCOLS IN MOLECULAR BIOLOGY*, John Wiley and Sons, Inc., Media PA (1988)
Bowman, R. D., and Davidson, N., *Biopolymers* 11:2601–2624 (1972).
Cavalieri, L. F., and Rosenberg, B. H., *J. Amer. Chem. Soc.* 81:5136–5139 (1959).
Davison, P. F., *Proc. Natl. Acad. Sci USA* 45:1560–1568 (1959).
Davison, P. F., *Nature* 185:918–920 (1960).
Deininger, P. L., et al., *Anal. Biochem.* 129:216–223 (1983).
Fodor, S. P. A., et al., *Science* 251:767–773 (1991).
Frenkel, J., *Acta Physiochim. URSS* 19:51–76 (1994).
Hershey, A. D., and Burgi, E., *J. Mol. Biol.* 2:143–152 (1960).
Larson, R. G., *Rheol. Acta* 29:371–384 (1990).
Lipshutz, R. J., et al., *Biotechniques* 19:442–447 (1995).
Maniatis, T., et al., in *MOLECULAR CLONING: A LABORATORY MANUAL* (Cold Spring Harbor Press, Cold Spring Harbor, N.Y.) (1982).
Reese, H. R., and Zimm, B. H., *J. Chem. Phys.* 92:2650–2662 (1990).
Riles, L., et al., *Genetics* 134:81–150 (1993).
Rosenberg, H. S., and Bendich, A., *J. Amer. Chem. Soc.* 82:3198–3201 (1960).
Rosenberg, H. S., and Studier, F. W., *Biopolymers* 7:765–774 (1969).
Sambrook, J., et al., In *MOLECULAR CLONING: A LABORATORY MANUAL*, Cold Spring Harbor Laboratory Press, Vol. 2 (1989).
Wiest, J. M., et al., *J. Chem. Phys.* 90:587–594 (1989).

BACKGROUND OF THE INVENTION

Several methods have been described for random fragmentation of DNA. These methods, often used for library preparation and subcloning prior to DNA sequence analysis, include passage through the small orifice of a hypodermic needle (Davison, 1959, 1960) or of a high pressure spray atomizer (Cavalieri and Rosenberg, 1959), sonic treatment (Deininger, 1983), stirring in a blender (Hershey and Burgi, 1960; Rosenberg and Bendich, 1960), as well as partial digestion by restriction endonucleases (Maniatis, et al., 1982) or treatment with DNase I in the presence of manganese ions (Anderson, 1981). While all of these methods have been used successfully to prepare random DNA fragments for further manipulation and analysis, each has difficulties and limitations. Shearing by passage through a hypodermic needle or by stirring fail to generate small enough fragments for efficient cloning and sequencing.

Sonication is difficult to reproduce, requires relatively large amounts of DNA, and yields a relatively broad size distribution and, hence, a low yield of fragments being of use for cloning and sequencing. Low cloning efficiencies have also been attributed to damage inflicted on DNA by the action of atomic oxygen, hydrogen peroxide and other free radicals, which are known to arise as a result of chemical reactions, associated with cavitation phenomena, due to ultrasonic waves.

Enzymatic methods, such as the use of restriction enzymes, also have a number of disadvantages. First, some regions of DNA sequence have very few restriction sites and would be under-represented in the resulting clone banks. Second, several different restriction enzymes are necessary to obtain fragments which overlap each other properly to complete the DNA sequence analysis. Third, many restriction fragments are quite small and, hence, yield only very little information upon sequencing. DNase I overcomes some of these difficulties, as it cleaves with very little sequence specificity. Due to the wide size distribution of the resultant fragments, however, the yield of fragments having the appropriate length for cloning and subsequent sequence analysis tends to be very small.

The present invention overcomes disadvantages of previous methods by providing an apparatus and methods for producing randomly-cleaved, efficiently-clonable polynucleotide fragments having narrow size distributions (about 2-fold difference between the longest and shortest fragments) with a selected mean (ranging from about 200 base pairs (bp) to about 20,000 bp for double-stranded (ds) polynucleotides; about half of those values for single-stranded (ss) polynucleotides).

SUMMARY OF THE INVENTION

In one aspect, the present invention includes a shearing assembly suitable for shearing long polymers, such as polynucleotides (e.g., DNA) into smaller fragments, whose lengths form a defined distribution with a selected mean. In the case of ds polynucleotide fragments, the mean is typically between about 200 and about 20,000 base pairs (bp). In the case of ss polynucleotide fragments, the mean is typically between about 100 and about 10,000 base pairs (bp). The shearing assembly is particularly well-suited for generating narrow (~2-fold) distributions of polynucleotide fragments, where over about 85% of all fragments are within a factor of two of one another with respect to size.

The shearing assembly includes a first capillary having an inlet end and an outlet end. An orifice, having a diameter of between about 0.001 inch (") and 0.005", is positioned at the outlet end. In one embodiment, the orifice is the channel of a second capillary attached at the outlet end of the first capillary. Since the second capillary is functioning as the orifice, it has an inner diameter that is at least about a factor of two smaller that the inner diameter of the first capillary; preferably, the diameter of the second capillary is at least about 3 times smaller than that of the first capillary. For efficient generation of fragments below about 4,000 base pairs, the diameter of the second capillary is preferably at least about 5 times smaller than the diameter of the first capillary. The transition in I.D.s from the first capillary to the orifice is preferably abrupt, rather than gradually tapering to a smaller diameter.

Exemplary orifices according to this embodiment of the invention are capillaries made from polyetheretherketone (PEEK) or stainless steel tubing having an inner diameter of 0.0025".

In some instances described below, the shearing assembly refers to only a single capillary. In those cases, it will be understood that the single capillary referred to corresponds to the "first" capillary described above, and that the "second" capillary, when present, is indicated simply as the "orifice".

In another embodiment, the orifice is a hole in a disk positioned at the outlet end of the first capillary. An exemplary orifice according to this embodiment of the invention is a ruby disk with a 0.002" or 0.0025" diameter hole.

The shearing assembly may also include a means for inducing extensional flow, or for "conditioning" the flow of the suspension of polynucleotide fragment upstream of the orifice. According to the teachings herein, this feature promotes the alignment of polynucleotide fragments in the suspension in the direction of the flow, thus facilitating their breakage when they enter the orifice. A preferred means for inducing extensional flow is a "tee" (T), wherein streams of the suspension are directed into the opposing (horizontal) arms of the tee, and the flow is conditioned as it changes direction to flow down the vertical arm. Tees suitable for use with the methods of the present invention typically have an internal volume of between about 0.5 $\mu$l and about 5 $\mu$l and an internal tubing diameter of between about 0.01" and about 0.05". An exemplary tee, whose vertical arm constitutes the first capillary of the shearing assembly, has an internal volume of about 0.62 $\mu$l. The vertical arm of this tee has an inner diameter of about 0.015".

When included in the shearing assembly, the mechanism for conditioning the flow (e.g., tee) is typically situated at the inlet end of the first capillary, such that the suspension is "conditioned" as it flows through the first capillary and into the orifice. Because the flow tends to lose its "extensional" character with distance downstream of the point at which extensional flow is induced, the orifice is preferably located within about 5 cm, and, preferably, within about 5 mm, of the point at which extensional flow is induced (e.g., between about 1 mm and about 5 mm from the means). In one exemplary embodiment, described herein, the orifice is located about 1.8 mm from the point at which extensional flow is induced (in this case, about 1.8 mm from the center of the junction of the horizontal and vertical members of the tee). Note that in this embodiment, the vertical member of the tee constitutes the capillary between the point at which extensional flow is induced and the orifice.

The shearing assembly is typically part of a larger apparatus useful for shearing polynucleotide chains. In addition to the shearing assembly, the apparatus typically contains a pump, or pumping means, effective to pass the suspension of polynucleotide fragments through the shearing assembly at the desired flow rates (at least about 1 ml/min). Preferably, the pump should be able to achieve flow rates of up to about 10 ml/min, more preferably, up to about 25 ml/min. In one embodiment, the pump is a high pressure liquid chromatography (HPLC) pump. In another embodiment, the pump is a syringe pump.

The apparatus also preferably contains a repeat pass means for passing the suspension through the shearing assembly for a selected number of passes. In one embodiment, this is accomplished by recirculating the suspension through the shearing assembly via unidirectional flow through a closed loop.

In another embodiment, repeated passes are made using a reciprocating motion, where the suspension is passed back and forth through the shearing assembly by alternating the flow of the suspension. The alternating flow can be set up by alternate application of pressure or suction on one side of the orifice. In such an application, however, the amount of suction applied is preferably maintained below a value above which bubbles would form in the system. Since the rate at which solution is passed through the shearing assembly in response to such low suction is too small to result in substantial shearing, essentially all the shearing will occur during the "pressure" cycle. Accordingly, one pressure/suction cycle, while moving the suspension through the shearing assembly twice, typically results in only one "functional" pass of the suspension through the shearing assembly.

The apparatus may also include ports for the injection of a polynucleotide sample (sample port) and for its collection (collection port). The amount of sample collected may constitute a small portion of the suspension (e.g., to assay the degree of shearing after a selected number of passes), or it may constitute the entire suspension (e.g., collected at the completion of a run). The inflow and outflow ports may be distinct, or they may be one and the same.

The apparatus also typically contains valves, which may be switched to allow, for example, the recycling of the sample, collection of the sample, the introduction of various solvents or buffers to the sample, and the like. Further, the apparatus may be automated, e.g., outfitted with an electric valve, an autosampler for injecting the samples and a fraction collector for collecting the fragments, and can be constructed such that the sheared DNA molecules may be loaded directly on a chromatographic column for further size fractionation. An automated apparatus is typically controlled by a computer running a software program that lets the user set the desired run parameters, and that then controls the relevant parts of the apparatus.

In another aspect, the present invention includes a method of producing a defined size distribution of polynucleotide fragments. In the case of double-stranded DNA, the distribution has a selected mean size range between about 200 and about 20,000 base pairs (bp). In the case of single-stranded DNA, the distribution has a selected mean size range between about 100 and about 10,000 base pairs (bp). The distribution is preferably such that over about 85% of the fragments making up the distribution are within a factor of two of one another in length.

The method includes the steps of passing a suspension of polynucleotide fragments through the shearing assembly described above, and by such passing, shearing the fragments into fragments having a size range about half of the size range before the passing. The passing is continued until the polynucleotide fragments in the suspension attain a desired size distribution.

The method may be used to shear polynucleotide fragments of essentially any size; experiments performed in support of the present invention have shown that dsDNA fragments as large as 3 megabases (mb) can be successfully cleaved and reduced to a distribution of fragments having a selected mean between about 200 and 20,000 bp and about a 2-fold difference between the largest and smallest fragments. Accordingly, the method is applicable anytime that it is desired to obtain a distribution of fragments with a smaller mean size than the starting fragments. The method may also be employed simply to narrow the breadth of a starting distribution of DNA sizes. For example, the method may be applied to transform a distribution of fragments ranging from about 2 kbp to about 20 kbp to one ranging from about 2 kbp to about 4 kbp.

The parameters of operation of the shearing assembly are set by the user such that the desired size distribution of fragments is obtained. The desired distribution is obtained by recirculating or reciprocating the polynucleotide fragment suspension through a shearing assembly containing a selected orifice at a selected flow rate until the character (mean, breadth) of the distribution stabilizes, i.e., until the mean and standard deviation of the distribution approach their respective asymptotic values such that additional passes through the shearing assembly do not further change the distribution character. According to the teachings herein, the asymptotic value of the distribution breadth is a 2-fold distribution.

Other factors being equal, the higher the flow rate through the shearing assembly, the smaller the mean size of the sheared fragments. The method is practiced using flow rates of at least 1 ml/min; preferably at least about 3 ml/min. Flow rates between about 3 ml/min and about 12 ml/min are suitable for most applications, although generating distributions with a mean size of 200–500 bp may require flow rates as high as 20–25 ml/min. Specifically, it is contemplated that using a flow rate of about 23 ml/minute (which can be achieved using, for example, the extended flow range option available for the Waters Model 510 HPLC pump (Marlborough, Mass.)), ds polynucleotide fragments having a mean length of about 200 bp can be generated.

Similarly, other factors being equal, the smaller the size of the orifice, the smaller the mean size of the sheared fragments. The method is typically practiced with orifice diameters between about 0.001" and about 0.005"; for the generation of fragments less than about 4,000 bp in length, the orifice diameter is preferably between about 0.001" and 0.003". An exemplary orifice has a diameter of 0.0025".

The flow rate and orifice diameter are determined by the practitioner of the invention, according to the teachings herein, to generate a desired size distribution of polynucleotide fragments. For instance, as described in Example 2, using the HPLC-based apparatus with a "tee" shearing assembly detailed below, ds polynucleotide fragments having a mean size of about 500 bp can be generated using a flow rate of about 8.6 ml/min through an orifice having an internal diameter of about 0.0025". Distributions of polynucleotide fragments with longer mean lengths can be generated by reducing the flow rate (e.g., FIG. 2) and/or increasing the diameter of the orifice.

In one general embodiment, the method is applied to polynucleotide fragments that are either single-stranded or double-stranded DNA fragments. A type of DNA that is particularly amenable to shearing by the above method is genomic DNA (e.g., human genomic DNA). Methods for the isolation of genomic DNA are well known in the art (e.g., Sambrook, et al., 1989; Ausubel, et al., 1988). If no special precautions are taken to preserve the integrity of the genomic DNA during isolation, the isolated DNA is typically composed of fragments between about 10 kb and about 50 kb. In other embodiments, the method is applied to cDNA fragments and/or RNA fragments.

As stated above, the method is useful for shearing both single as well as double-stranded polynucleotides. It will be understood that for any specific combination of parameters relating to the shearing assembly (e.g., orifice size, flow rate, etc.), single stranded polynucleotides will be sheared to a distribution with a mean length that is about half of what it would be for double-stranded polynucleotides of the same type. This is due to the fact that it takes about twice as much force to shear a double-stranded polynucleotide as it does to shear a single-stranded polynucleotide.

In one general embodiment, the method is carried out using the apparatus illustrated in FIG. 1A having the shearing assembly illustrated in FIG. 2C. This combination has a total dead volume of about 1 ml. With this apparatus, the flow rate of the suspension through the shearing assembly is between about 1 ml/minute and about 10 ml/minute (with the extended flow range option is installed, the flow rate is between about 1 ml/minute and about 25 ml/minute.

These and other objects and features of the invention will become more fully apparent when the following detailed description is read in conjunction with the accompanying drawings.

DETAILED DESCRIPTION OF THE INVENTION

I. Definitions

"orifice" is used in the present application to refer to a constriction in a tube or capillary effective to reduce the inner diameter of the tube or capillary by at least a factor of about 2; preferably al least about 4. Examples of an orifice include a hole in a disk positioned in a capillary, as well as a capillary with a small internal diameter connected to a capillary with a larger internal diameter.

A "two-fold size distribution" of polynucleotide fragments, or a "size range where the largest polynucleotide fragment in the size range is about twice as large as the smallest polynucleotide fragment in the size range", are understood to mean mixture of polynucleotide fragments where over about 85% of the fragments are of a size where the largest polynucleotide fragment in the size range is about twice as large as the smallest polynucleotide fragment in the size range.

II. Apparatus Containing Shearing Assembly

Figure 1A:
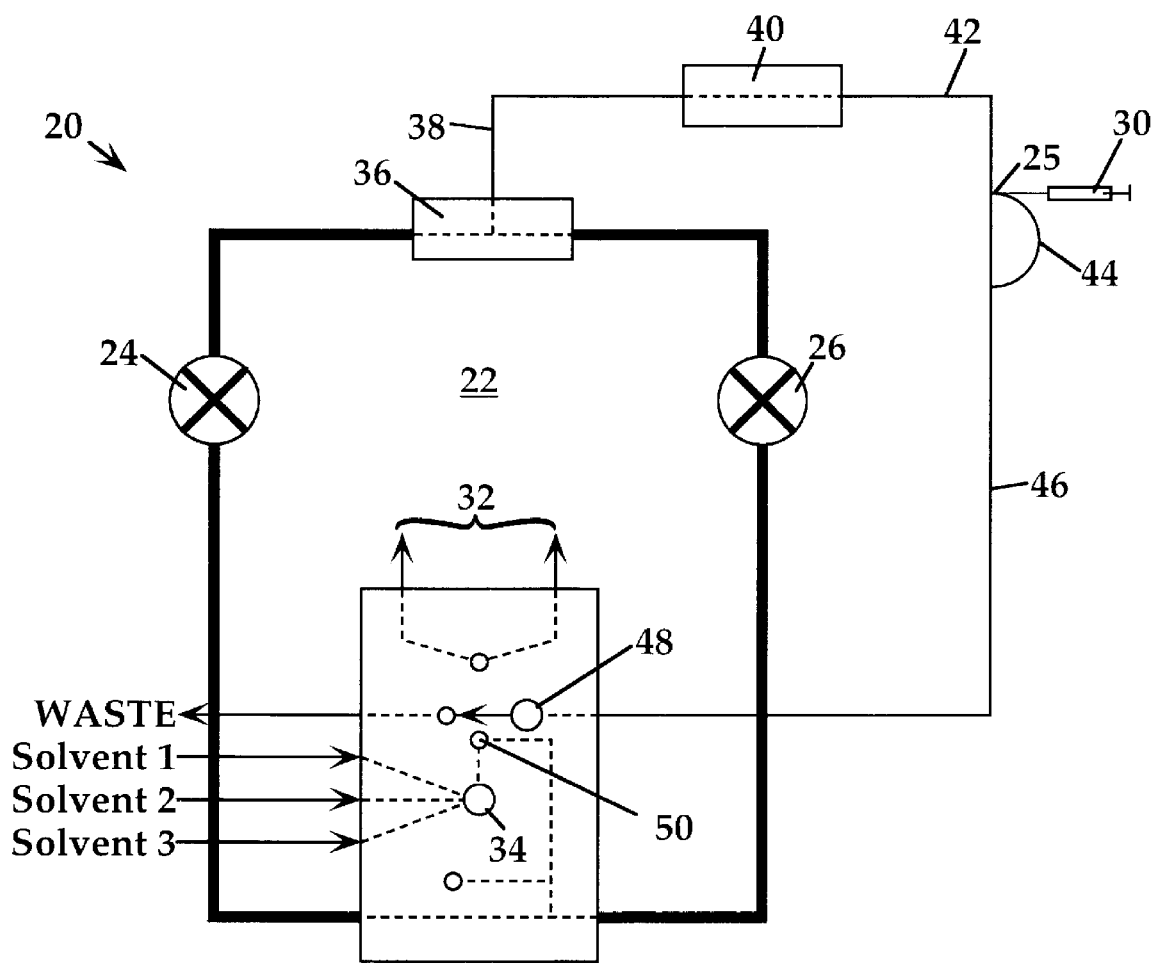
FIG. 1A shows a schematic of one embodiment of an apparatus suitable for shearing double- or single-stranded polynucleotides.

In one general embodiment, the present invention includes an apparatus containing a shearing assembly for shearing polynucleotide chains. An exemplary embodiment of such an apparatus is illustrated in FIG. 1A. The apparatus 20 is constructed around a high-performance liquid chromatographic pump 22, such as a Waters 510 HPLC pump. In addition to the shearing assembly 36, the apparatus 20 contains a left pump head 24 and right pump head 26 effective to force a suspension of polynucleotide fragments to pass through the shearing assembly at desired flow rates (e.g., between about 1 and 10 ml/min; up to about 23 ml/min with the extended flow range option). Downstream of the tee shearing assembly is a pressure transducer 40.

Also included in the apparatus is a port for the injection of a polynucleotide sample, such as sample port 30. The polynucleotide sample suspension is provided in this embodiment by syringe 30. Port(s), such as ports 32, are also typically provided for the collection of sample after it has passed through the shearing assembly for a selected number of passes. The apparatus also contains a valve or valves (e.g., solvent select valve 34, valve 48), which may be switched to allow, for example, the recycling of the sample (for another pass), collection of the sample, the introduction of various solvents or buffers to the sample, the drawoff of solvents, and the like.

With continued reference to FIG. 1A, sample can be recirculated through the system by routing it via tubing 38, 42 and 46 (e.g., PEEK tubing) to valve 48, which can be set to "Recycle" position 50, enabling sample to flow into the inlet ends of pumps 24 and 26 and be passed again through shearing assembly 22. Alternatively, valve 48 can be set to allow collection of the sample via ports 32, or to drain the system into "waste".

Figure 1B:
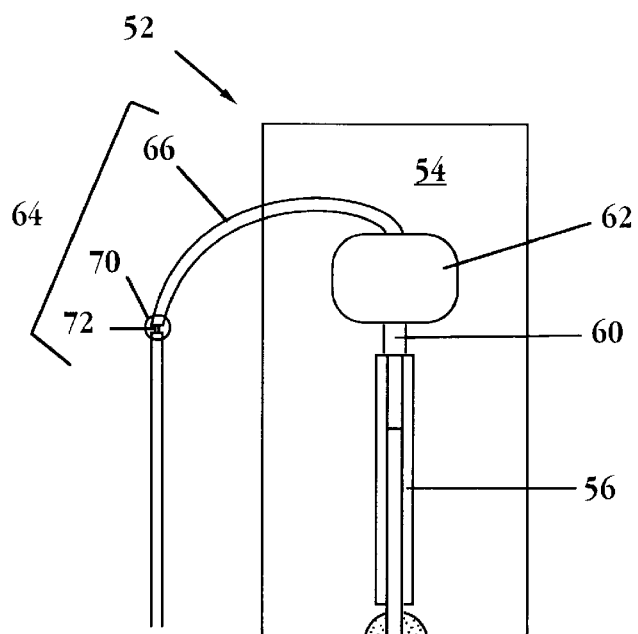
FIG. 1B shows a schematic of a second embodiment of an apparatus suitable for shearing double- or single-stranded polynucleotides.

Another embodiment of the present invention is shown in FIG. 1B. The apparatus 52 is based on a Cavro XL 3000 Digital Syringe Pump 54, which has an adjustable flow rate with a maximum of about 10.3 ml/min. The pump is shown with a syringe 56 and plunger 58 (e.g., a Hamilton 1750XC 500 μl syringe; Hamilton, Reno, Nev.) connected to a driving motor. The outlet of the syringe 60 is connected through an input port of an interface block or valve 62 (e.g., a V101-L valve) to the shearing assembly 64, which contains a capillary or tubing, such as tubing 66 linked to a second portion of tubing 68 by a union 70. A disk 72 with a hole in the center, comprising the orifice, is mounted inside the union. The dead volume in this configuration (volume of sample suspension that does not reach the orifice when the syringe is completely depressed) is about 45 μl.

Note that the shearing assembly in this apparatus is suitable for operation via a "reciprocating" passing of the polynucleotide fragment suspension through the assembly, with the syringe and plunger on the pump providing the pumping means.

The apparatus shown in FIG. 1B requires that the sample be loaded directly into the syringe, necessitating partial disassembly of the apparatus. More convenient sample loading can be achieved using an apparatus with a sample inlet port, such as the apparatus illustrated in FIG. 1C. The apparatus 80 is also based on a Cavro XL 3000 Digital Syringe Pump 82. Here, however, the sample is introduced through an inlet 84 that is in communication with valve 86, such as an Upchurch 90° 500 psi valve (V-101L). The valve is constructed to, upon actuation, place the sample into a channel in communication with both the syringe 88 and tubing 90, while at the same time blocking access to the sample inlet 84. The shearing assembly 92 in this embodiment contains an orifice formed of a capillary 94, typically between about 1.5 mm and about 6 mm in length. As above, the capillary 94 can be connected to tubing 90 and 96 by trapping the capillary between tubing 92 and 94 in a tubing union.

Figure 1C:
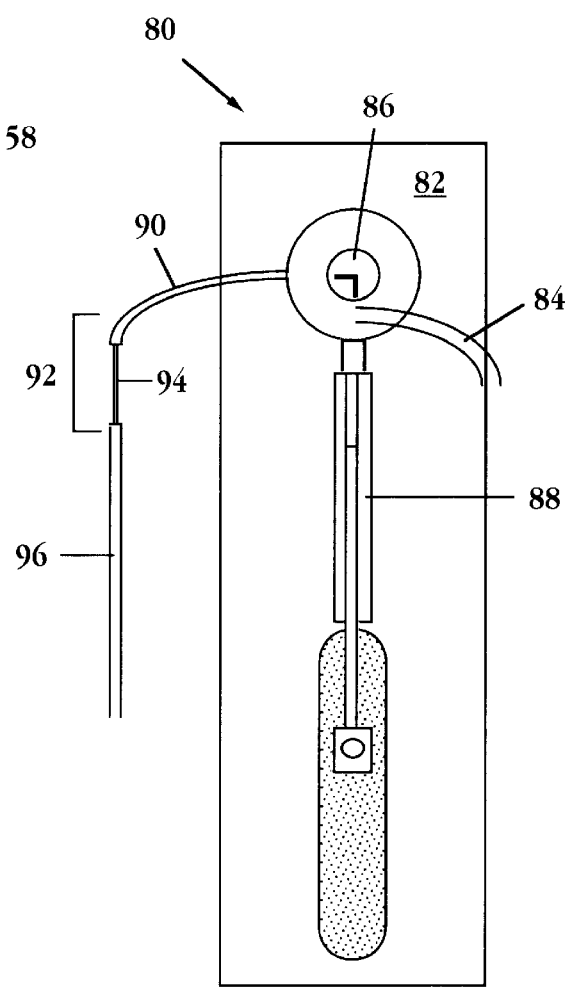
FIG. 1C shows a schematic of a third embodiment of an apparatus suitable for shearing double- or single-stranded polynucleotides.
Figure 1D:
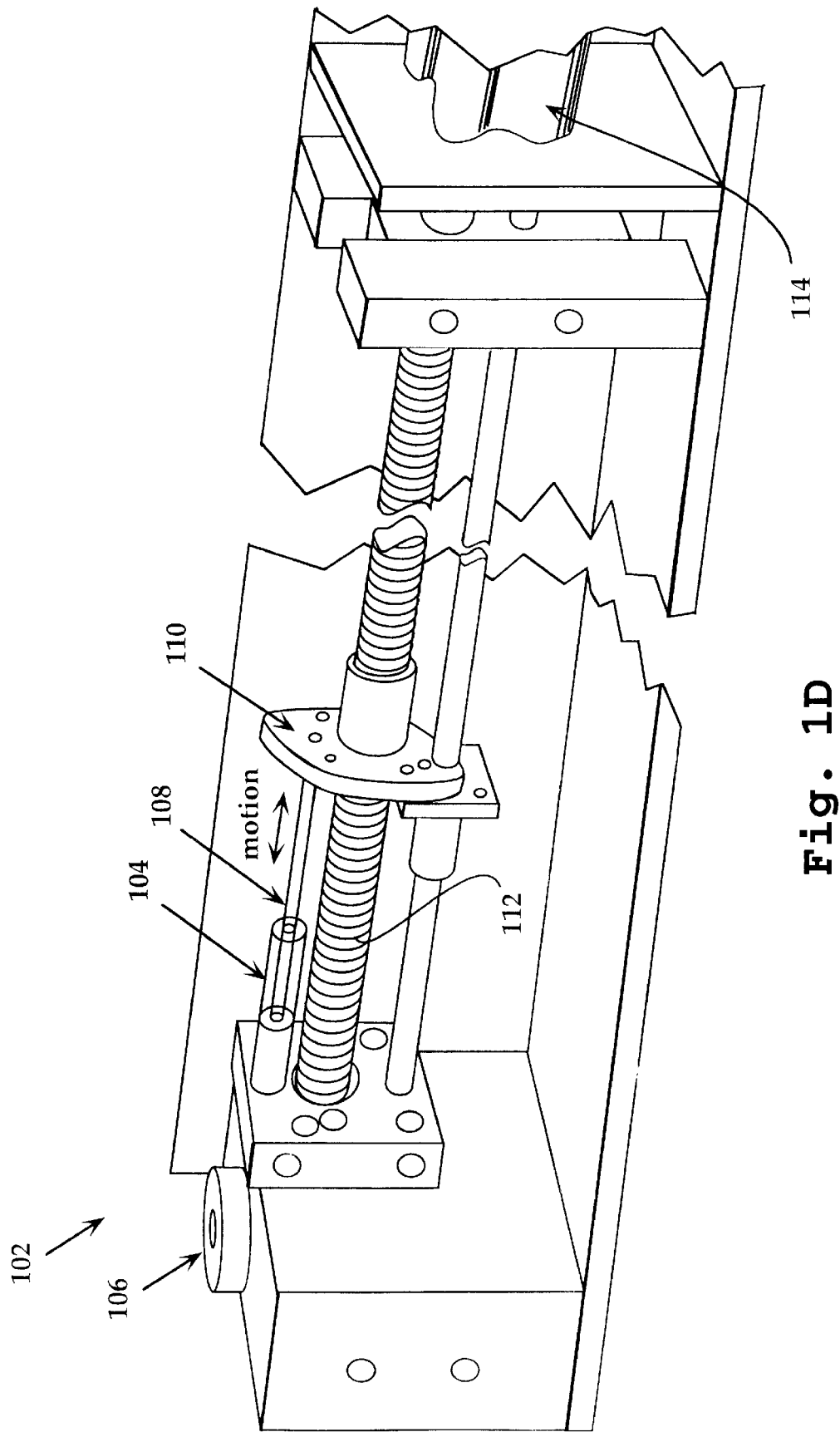
FIG. 1D shows a schematic of a fourth embodiment of an apparatus suitable for shearing double- or single-stranded polynucleotides.

A third embodiment is shown in FIG. 1D. The apparatus 102 also uses a syringe 104 for passing a suspension of polynucleotide fragments through the shearing assembly (not shown) via a valve 106 for the introduction of a sample into the system. The syringe is actuated by plunger 108 connected to transfer plate 110 threadably mounted onto lead screw 112. The lead screw 110 is in turn actuated by motor 114.

Figure 2A:
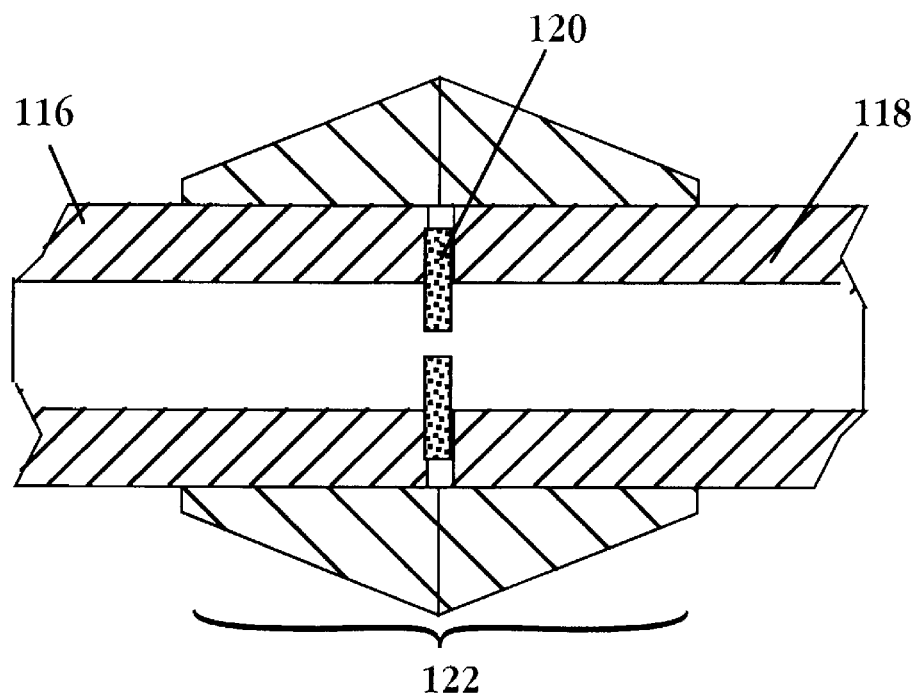
FIG. 2A shows a schematic of a shearing assembly containing an orifice formed of a disk.

FIGS. 2A, 2B, 2C and 2D show embodiments of shearing assemblies according to the invention. FIG. 2A shows a shearing assembly such as was employed in the apparatus in FIG. 1B. The orifice 120, e.g., a 0.002" ruby orifice (Byrd Precision, Waltham, Mass.), is sandwiched between two segments of tubing 116, 118, such as 0.030" I.D., 1/16" outer diameter (O.D.) "TEFLON" tubing (Upchurch Scientific; cat #1520), inside a tubing union 122, such as a Tefzel Union (Upchurch, P-603), with PEEK nuts and ferrules (Upchurch, P-204X, P-200Nx).

Figure 2B:
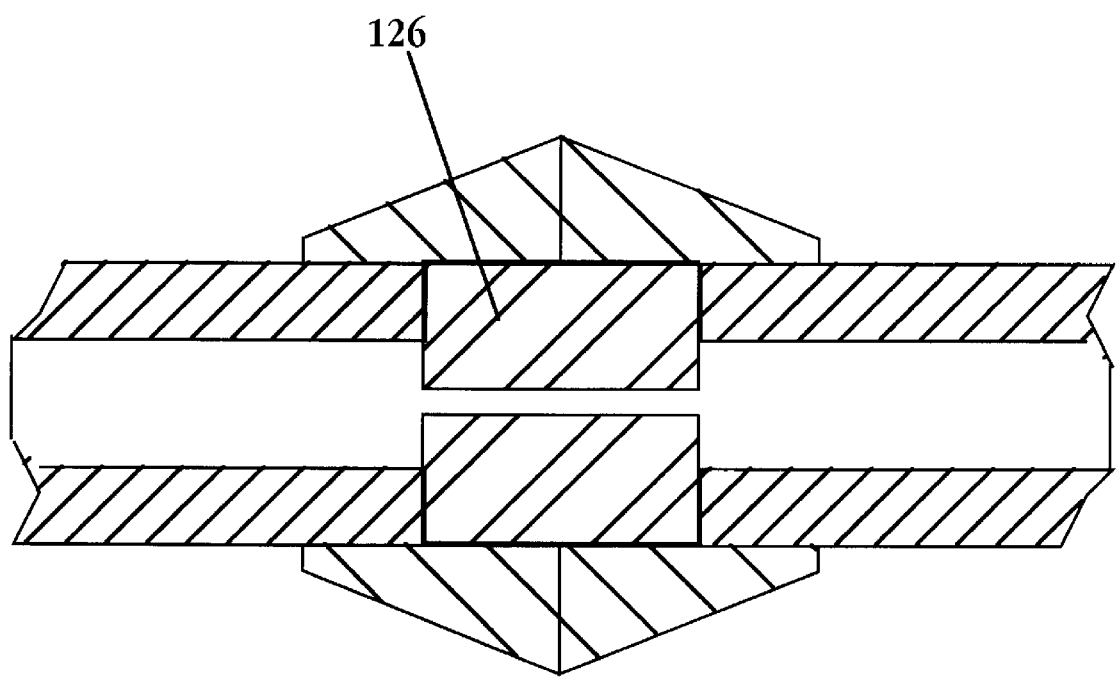
FIG. 2B shows a schematic of a shearing assembly containing an orifice formed of a capillary.

FIG. 2B shows a shearing assembly such as was employed in the apparatus in FIG. 1C. The shearing assembly is like the one described with respect to FIG. 2A, except that the orifice is a capillary 126 formed, e.g., from a segment of 0.0025" I.D., 1/16" O.D. PEEK tubing (Upchurch, 1560). Capillary orifices are typically between about 1 and 6 mm in length.

Figure 2C:
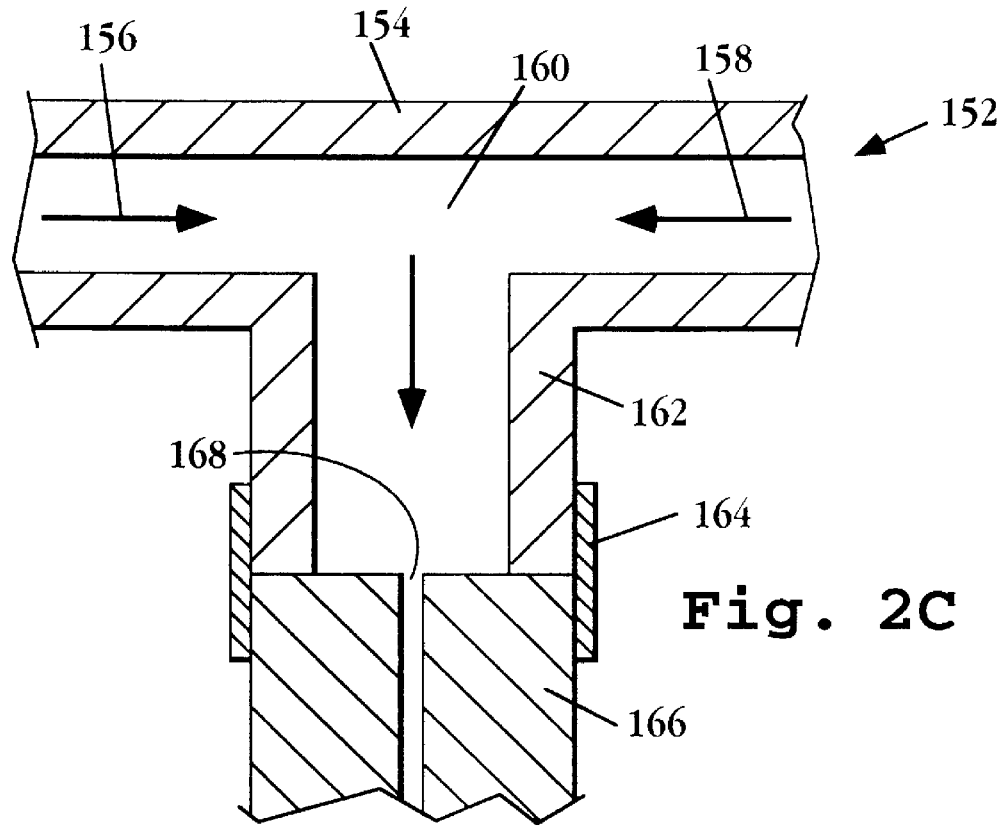
FIG. 2C shows a schematic of a shearing assembly in the form of a tee suitable to induce extensional flow and an orifice formed of a capillary with a narrower inner diameter.
Figure 2D:
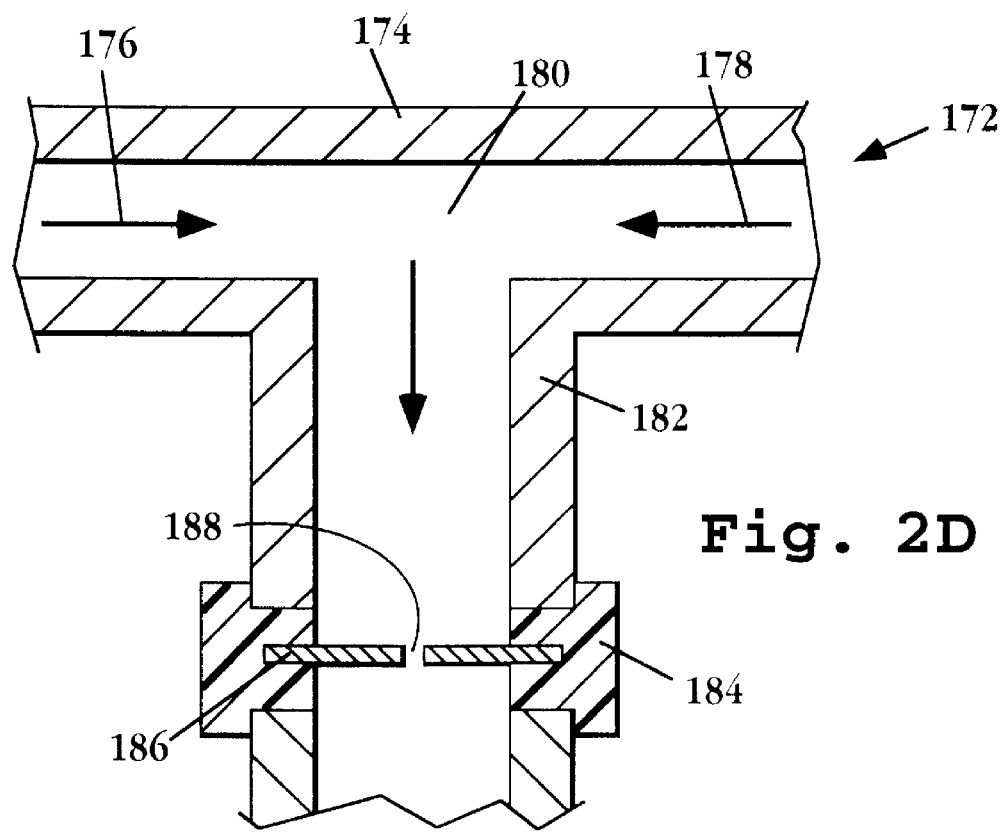
FIG. 2D shows a schematic of a shearing assembly in the form of a tee suitable to induce extensional flow and an orifice formed of a disk.

Examples of shearing assemblies suitable for use with, e.g., the apparatus shown in FIG. 1A, are illustrated in FIGS. 2C and 2D. FIG. 2C shows a "tee" 152 where streams 156, 158 of the suspension are directed into the opposing (horizontal) arms 154 of the tee, and the flow is conditioned as it changes direction 160 to flow down the vertical arm 162. The outlet of the vertical arm is connected to the a second capillary 166 attached via an external coupling 164. The second capillary has an inner diameter 168 that is considerably smaller that the inner diameter of the first capillary, and accordingly, constitutes an orifice. Note that in this embodiment, as well as the one described below with respect to FIG. 2D, the vertical arm of the tee acts as the capillary connecting the means for inducing extensional flow with the orifice.

FIG. 2D shows a similar tee 172 to that shown in FIG. 2C. Here again, streams 176, 178 of the suspension are directed into the opposing (horizontal) arms 174 of the tee, and the flow is conditioned as it changes direction 180 to flow down the vertical arm 182. The outlet of the vertical arm is connected to a disk-retaining assembly 184 containing a disk 186, such as a ruby disk, with a hole 188 in the center serving as the orifice.

Operation of a polynucleotide shearing apparatus of the present invention can be facilitated by controlling the various steps in the operation of the apparatus (i.e., sample loading, valve control, pump control, washing, etc.) with a computer, such as an IBM-compatible PC. The computer typically contains a standard interface board which is connected to the device via, e.g., a ribbon cable. The computer can be set up to run a software program which enables the user to set the relevant control parameters for a number of different functions, such as wash, load, shear, expel, and rinse steps. Software that allows for scripted protocols, similar to the SYGI software that controls the Beckman Biomek robot, is particularly suitable for use with the apparatus.

In operation, a suspension of polynucleotides is introduced into an apparatus of the present invention. This is typically accomplished either by switching a valve and programming the pump to draw in the sample or by removing the syringe from the device and putting sample directly into the syringe. After the sample is introduced, the suspension is passed through the shearing assembly, either in a recirculating manner via a closed loop, or in a reciprocating manner. Recirculating shearing is discussed in detail in the Materials and Methods section, below.

In a reciprocating syringe-based system, the computer is typically programmed to (i) expel the sample suspension from the syringe through the orifice at the shearing speed, and then to (ii) slowly draw the sample back into the syringe at a rate slow enough that air bubbles are not precipitated by a sudden vacuum within the sample suspension. These steps are repeated for a selected number of cycles, typically between about 10 and 50, often between about 15 and 30.

Following the shearing cycles, the sample suspension is expelled as required either by switching the valve and programming the pump to expel the sample or by removing the syringe from the pump. The apparatus is then typically washed by repeatedly drawing in and expelling a wash solution to prevent contamination of the next sample. An exemplary wash protocol is washing with solutions of HCl and NaOH, followed by rinses with distilled, deionized water.

III. Production of Defined Size Distributions of Polynucleotide Fragments

In one aspect, the present invention provides a method of producing a defined size distribution of polynucleotide fragments, such as DNA fragments. The distribution is preferably narrow, where more than about 85% of all fragments were within a factor of two of one another with respect to size. This type of distribution is termed herein as a "two-fold" distribution. The mean size of such a distribution can be determined from data showing the lengths of the fragments in the distribution (e.g., images of ethidium bromide-stained gels) by adding the sizes of the smallest and largest fragments in the distribution, and dividing by 2. For example, with reference to lane 9 in FIG. 2, it can be appreciated that the smallest fragments are about 400 bp, and the largest fragments are about 1000 bp. Accordingly, the mean of this distribution is about 700 bp.

The mean size of the distributions obtained depends primarily on the diameter or size of the orifice, the flow rate, the ionic strength, the length of the orifice (if it is a capillary as opposed to a disk) and on the number of passes through the shearing assembly, as exemplified in Examples 1–4. As is detailed more fully below, the 2-fold distribution arises as follows: The polynucleotides become extended as they enter the orifice, and experience a shear force that, if strong enough to break a particular polynucleotide, tends to break it at a point that is at about the middle of the molecule (±12%). As the suspension of polynucleotides is recirculated through the system, all chains longer that a "critical" length tend to get broken in two. Chains shorter than this critical length remain intact, since the shear force is not great enough to break the internucleotide bonds.

The net shear force experienced by the polynucleotide chain is determined primarily by the diameter of the orifice, by the flow rate into and through the orifice, and, to a lesser extent, by the length of the orifice in capillary orifices. The smaller the orifice, the greater the shear; the higher the flow rate, the greater the shear; and the longer the capillary, the greater the shear. It will be appreciated, however, that if the suspension is passed through the shearing assembly only once or a few times, the mean of the fragment size distribution will be greater than if it is passed through a sufficient number of times to allow breakage of all strands longer than the critical length.

The number of passes required to reach such a "steady state" of fragment sizes is about 10 to 50; under most conditions, about 15 to 30. The number of passes also depends to some extent of the size of the starting distribution (i.e., megabase range DNA may take several more passes than kilobase range DNA), although experiments performed in support of the present invention indicate that 3 megabase DNA can be cleaved to a 2-fold distribution with a mean of about 3 kb in as few as 20 passes through an orifice 0.0025" in diameter at a flow rate of about 6 ml/min.

The "length" of the orifice (with a "zero" length orifice exemplified by a disk orifice, and an orifice of finite length exemplified by a capillary) has a moderate effect of the shearing results, with longer orifices resulting in a smaller mean fragment size. For example, at a flow rate of 6 ml/min through a 3 mm section of 0.0025" ID tubing, the mean fragment size is about 2.9 kb. Increasing the tubing size to 6 mm reduces the mean size to about 2.4 kb.

In a syringe-based apparatus, fluid remaining between the head of the syringe and the orifice (i.e., the "dead volume") is not sheared in that pass. The effect of the dead volume becomes apparent only as the total sample volume approaches the dead volume, and may be mitigated by increasing the number of shearing passes or by drawing the sample further into the syringe between passes. Both of these methods increase the likelihood that all DNA molecules in the sample will pass through the orifice enough times to result in a 2-fold distribution.

DNA concentrations as high as 6 $\mu$g/ml do not seem to affect either the mean of or the number of passes required to reach a 2-fold distribution. Similarly, changes in temperature to just below the DNA melting temperature had no significant effect on the results.

The present method is particularly amenable to the shearing of genomic DNA. For example, experiments performed in support of the present invention demonstrate that even broad starting distributions of fragment sizes, such as may be found in genomic DNA preparations, can be sheared into the narrow 2-fold size range distributions using approximately 20 passes as described above.

The polynucleotides in the suspension may be derived from a variety of sources. For example, as stated above, the fragments may comprise total genomic DNA (e.g., human genomic DNA). The fragments may also represent specific polynucleotide populations. For example, if an unknown gene has been localized to a particular yeast artificial chromosome (YAC) or cosmid, the insert DNA may subjected to the shearing methods described herein to generate a set a fragments suitable for subcloning for the purpose of more detailed mapping or sequencing.

The suspension may be passed through the assembly only once (e.g., as described in section C of the Materials and Methods), or more than once (e.g., as described in section B of the Materials and Methods). As discussed above, by passing the suspension through the shearing assembly multiple times (e.g., by recirculating it through a loop or reciprocating it through a region containing such an assembly), it is possible, according to the teachings herein, to generate size distributions with mean fragment sizes defined by the static parameters of the shearing apparatus (i.e., orifice diameter, flow rate, and length of orifice).

Samples of the suspension may be analyzed by, for example, agarose gel electrophoresis, to determine the number of passes through the assembly to attain a distribution having the desired mean fragment size.

IV. Mechanics of Polynucleotide Shearing

The physics of polymer stretching and breakage have been described (see, e.g. Reese and Zimm, 1990; Larson, 1990; Wiest, et al., 1989). It appears that while linear polymer (e.g., DNA) molecules are in a coiled state in the absence of flow, or in sufficiently weak flows, their central portions disentangle, as soon as the critical velocity gradient is reached, and become more and more straightened out along the direction of flow at the expense of the two end portions which remain curled. This non-uniform stretching of polymers, with a taut central portion and two randomly coiled end portions, is thought to occur because the viscous pull due to extensional flow is not uniform along the length of the chain, but roughly parabolic, being zero at the ends and maximum in the middle. This also accounts for the experimental observation that the chain scission in shear degradation typically occurs at about the midpoint of the chain. Rupture of the chain theoretically occurs when this force becomes comparable to the bond strength.

V. Utility

The apparatus and methods of the present invention may be used to generate DNA fragments for subsequent cloning, subcloning, sequencing, or the like. The fragments generated by the above-described methods are advantageous for use in subsequent molecular applications, since their ends are typically "clonable" without any additional enzymatic treatment. As described below, up to 40% of all fragments could be cloned directly, with only marginal improvements in clonability following end repair with Klenow, T4 polymerase or T4 polynucleotide kinase. Further, the sites at which the fragments are cleaved are not significantly biased toward any pattern of sequences or cleavage sites, and thus truly represent "randomly-cleaved" DNA.

The methods of the present invention also lend themselves readily to automation. For example, the apparatus containing the shearing assembly may be outfitted with an electric valve, an autosampler for injecting the samples and a fraction collector for collecting the fragments. Further automation may be achieved by reducing the dead volume of the system to less than about 40 $\mu$l, so that the sheared DNA molecules may be loaded directly on a chromatographic column for further size fractionation.

Another exemplary application for the methods and apparatus of the present invention is the generation of single-stranded polynucleotide fragments suitable for use with oligonucleotide probe arrays, such as arrays described by Fodor, et al. (1991), and Lipshutz, et al. (1995). Such arrays typically require single-stranded oligonucleotides on the order of 50 to 100 basepairs in length. According to the teachings herein, such oligonucleotides may be generated by, for example, denaturing genomic DNA and shearing it by passing a suspension containing the DNA through a shearing assembly at a flow rate of about 23 ml/min using an orifice with a diameter of about 0.0025" or smaller for a selected number of passes (e.g., 20–30 passes).

The following examples illustrate but in no way are intended to limit the present invention.

MATERIALS AND METHODS

Lambda DNA (Cat. No. 25250) and a 1 Kb DNA ladder (Cat. No. 15615) were purchased from GIBCO BRL/Life Technologies (Gaithersburg, Md.). Cosmid DNA from chromosome IV of *Saccharomyces cerevisiae* was isolated from an *E. coli* clone provided by Dr. Olson (Washington University, St. Louis, Mo.; Riles, et al., 1993).

The shearing buffer, the composition of which was identical to the buffer used to store $\lambda$DNA, contained 10 mM Tris-HCl, pH 7.4, 5 mM NaCl, and 0.1 mM $Na_2$ EDTA, and was prepared with Molecular Biology Reagents obtained from Sigma (St. Louis, Mo.). The same source of reagents was used to prepare TE-buffer (10 mM Tris-HCl, pH 8.0, 1 mM EDTA) and 5×gel loading solution (25% weight/volume [w/v] Ficoll, 0.05% w/v bromophenol blue, 0.05% w/v xylene cyanole FF).

A. Shearing Assembly and Apparatus

Shearing experiments were carried out using an apparatus (FIG. 1A) built around a Waters Model 510 HPLC pump (Marlborough, Mass.), which had been equipped with a three port inlet manifold assembly (Part No. 25712, Waters). Polyetheretherketone (PEEK) tubing ($\frac{1}{16}$" O.D.) and precut stainless steel capillary tubing ($\frac{1}{16}$" O.D.), as well as various unions and tees with the appropriate $\frac{1}{16}$" O.D. fittings were obtained from either Rainin Instrument Company (Woburn, Mass.) or Upchurch Scientific (Oak Harbor, Wash.).

FIG. 1A shows a schematic diagram of the apparatus used for shearing DNA in a recirculating point-sink flow system according to the methods of the present invention. The shearing assembly, explained in more detail with reference to FIG. 2C, was a 3-way tee connected to capillary tubing ($\frac{1}{16}$" O.D.; inner diameters ranging from 0.0025" to 0.04"). Unless otherwise indicated, the tubing was made of stainless steel. The apparatus also contained a manifold valve, which could be switched between WASTE, COLLECT and RECYCLE positions. In the RECYCLE mode, solvent returning from the shearing assembly was recirculated through the system and the pump did not draw solvent from the solvent reservoir.

The dead volume of the system in the RECYCLE mode was roughly 1 ml as determined by the photometric measurements of DNA dilution occurring over time. These measurements also revealed no significant losses of material during shearing, since the dilution factor did not change at various flow-rates.

The shearing buffer was vacuum filtered through a disposable sterile bottle top filter with a 0.22 μm cellulose acetate membrane (Part No. 25970-33, Corning Glass Works, Corning, N.Y.) and continuously degassed by passing it through two channels in series of a flow-through degasser placed in-line between the reservoir and the pump inlet (Cat. No. DG-1310, Rainin Instrument Company) to avoid the formation of air bubbles and to reduce the maximum residual dissolved oxygen in the solvent to less than 1 part per million (ppm).

The use of tubing having different inner diameters results in changes in back pressure and in the piston volume to be compressed before delivery can start, causing pressure-dependent deviations from the preset flow-rate. Accordingly, actual flow-rates for a given combination of tubing were determined by measuring the volume of solvent collected in a volumetric flask as a function of time. The volume flow per minute was calculated and indicated in relevant figure legends. DNA concentrations were determined using a Spectronic 1001 split-beam spectrophotometer (Bausch & Lomb Inc., Rochester, N.Y.).

B. Hydrodynamic shear breakage of DNA in recirculating mode

For shearing experiments carried out in the recirculating mode, 60–70 μl of a buffered solution containing 1–6 μg of DNA were loaded with a Hamilton microliter syringe (Reno, Nev.) into the 50 μl sample loop 44 of a seven-port sample injection valve (Rheodyne, Model 7725i, Cotati, Calif.) set to the LOAD position (FIG. 1A). The valve was then switched from LOAD to INJECT with the manifold valve in the RECYCLE position, and mobile phase was flushed through the loop for 30 sec at a flow-rate of 0.4 ml/min. The injection valve was then returned to the LOAD position in order to keep the internal volume as small as possible. Thereafter, the flow-rate was adjusted to the desired value. After the indicated period of time or number of passes, the manifold valve was switched to the COLLECT position and 700 μl of sheared DNA were collected.

The eluate was precipitated with 0.1 volume of 3M sodium acetate, pH 7.0, and 1 volume isopropanol. The sample was mixed thoroughly, incubated at −30° C. for at least 90 minutes and spun at 16000×g for 30 min. The pellet was washed twice with 75% ethanol, dried under vacuum and, finally resuspended in 16 μl of TE buffer and 4 μl of 5×sample loading solution (Ausubel, et al.).

Between shearing runs of DNA derived from the same source, the device was flushed with several milliliters of shearing buffer with the manifold valve in the WASTE position. Between the shearing of DNA from different sources, the device was rinsed extensively with 0.2M HCl followed by 0.2M NaOH in order to hydrolyze any remaining DNA in the device and thus minimize any possibility for carry-over. The device was then flushed extensively with shearing buffer to completely rinse out the sodium hydroxide solution prior to the next injection, to avoid denaturation of the DNA by the sodium hydroxide. If denaturation did occur, it could be detected as a second band of fragments at roughly half the expected size, since the band contained single-stranded DNA molecules that break twice as efficiently as double-stranded DNA.

C. Hydrodynamic shear breakage of DNA in a single pass

A 1/16" filter union with a removable 2-μm frit (Cat. No. ZUFR1F, Valco Instruments Co. Inc., Houston, Tex.) was attached to the column port of the sample injection valve by way of 5-cm stainless steel tubing with an internal diameter of 0.01". Identical tubing was then used to attach either a 0.62-μl stainless steel tee or a PEEK static mixing tee to the outlet of the filter union, with the other inlet of the tee having been plugged. A 4.8- or 10-cm PEEK tubing of 0.0025" I.D. was attached at the outlet of the tees. In order to avoid the loss of DNA at the outlet of the 0.0025" I.D. tubing, where a fine spray is otherwise formed, 5-cm stainless steel tubing of 0.046" I.D. was connected to the 0.0025" I.D. tubing by means of a PEEK union with a 0.02" I.D. thru-hole. This configuration enabled the formation of easily-collectable drops.

Alternatively, a 0.62-μl stainless steel tee or a 0.566-μl PEEK tee were used to split the flow, before converging it in a second 0.62-μl stainless steel tee or in the static mixing tee made of PEEK. The two tees were connected via 10-cm stainless steel tubing of 0.005" I.D. At the outlet of the second tee the aforementioned combination of 4.8-cm Peek tubing (0.0025" I.D.) and 5-cm stainless steel tubing (0.046" I.D.) were attached.

D. Agarose electrophoresis

Sheared DNA samples were separated on a 1% agarose slab gel ("SEAKEM GTG" FMC BioProducts, Rockland, Me.) in 45 mM Tris-borate buffer, pH 8.3, containing 1 mM EDTA. Separations were carried out in a horizontal agarose submarine unit (Model MGU-200T, C.B.S. Scientific Co., Del Mar, Calif.) at a constant voltage of approximately 115 V.

Sizes of the sheared DNA fragments were computed by digitizing images of ethidium bromide-stained agarose gels with the IS-1000 Digital Imaging System from Alpha Innotech Corp., San Leandro, Calif.. The image was calibrated with DNA fragments of known size, and then a cubic spline interpolation function was used to map digitized coordinates to fragment length in base pairs. The same device was used to determine the relative size distribution of the sheared fragments.

EXAMPLE 1

Kinetics of Breakage

Figure 3:
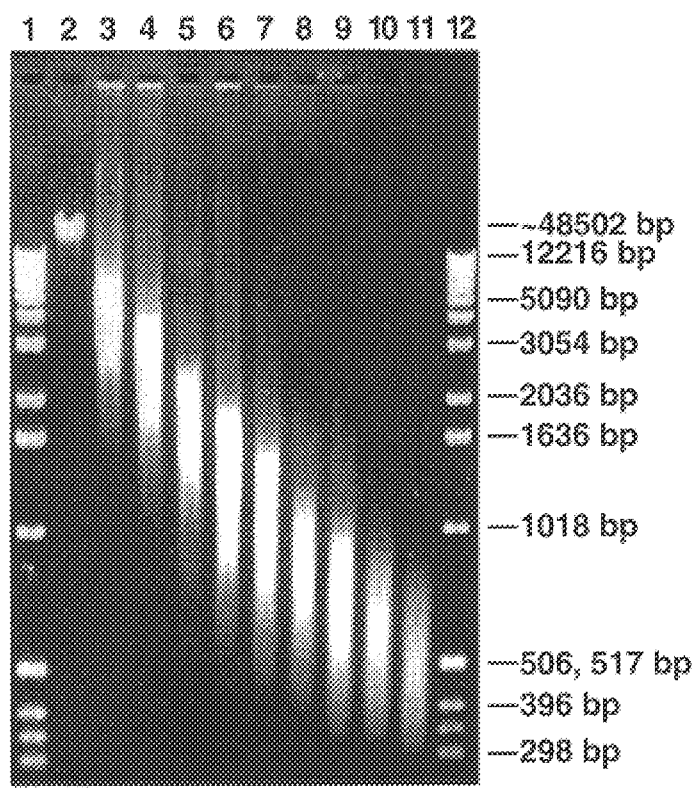
FIG. 3 shows an image of an agarose slab gel containing $\lambda$DNA sheared at various flow-rates using the apparatus shown in FIG. 1A equipped with a 0.62-$\mu$l stainless steel tee.

FIG. 3 shows the slab gel electrophoretic analysis of shear experiments carried out at various flow-rates ranging from 1.4 to 8.6 ml/min through the device of FIG. 1A, which was equipped with the 0.62-μl stainless steel tee, to the outlet of which a 4.8-cm PEEK tubing of 0.0025" I.D. had been attached.

Lanes 1 and 12: 1 Kb DNA ladder (0.5 μg each); lane 2: unsheared ξDNA (~0.1 μg); lanes 3–11: λDNA sheared at flow-rates of 1.35, 2.3, 3.2, 4.1, 5.0, 5.95, 6.9, 7.7, and 8.6 ml/min, respectively, for 8 min each. Amount of λDNA sheared: 4.08 μg each.

It is evident that, at a flow-rate of 8.6 ml/min, λDNA could be degraded to fragments ranging in size from roughly 300 to 600 base pairs. At lower flow-rates a less narrow size distribution was observed presumably due to the lower number of passes through the device.

Figure 4:
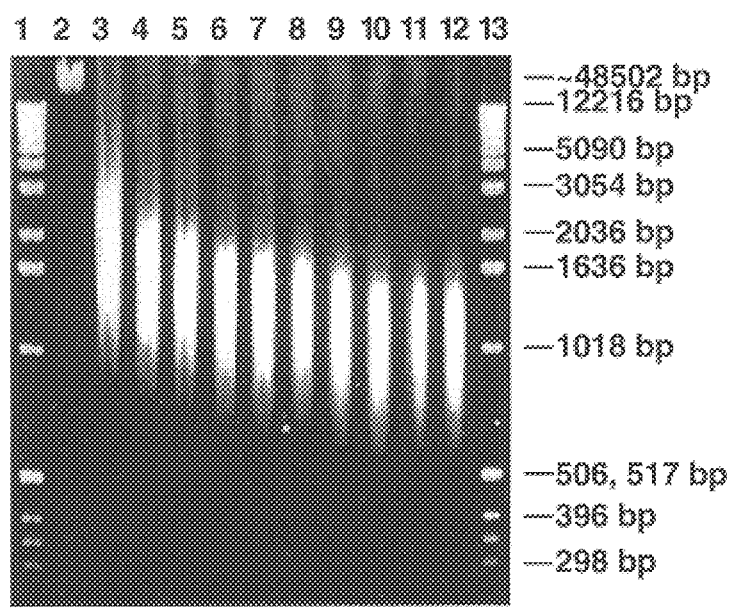
FIG. 4 shows an image of an agarose slab gel containing $\lambda$DNA sheared at a flow-rate of 5.0 ml/min for different periods of time using the apparatus used in FIG. 3.

FIG. 4 shows slab gel electrophoretic analysis of λDNA sheared at a flow-rate of 5.0 ml/min for different periods of time using the apparatus described above. Lanes 1 and 13: 1 Kb DNA ladder (0.5 μg each); lane 2: unsheared λDNA (~0.1 μg); lanes 3–12: λDNA (4.08 μg) sheared at a flow-rate of 5.0 ml/min for 0.33, 0.66, 1, 2, 3, 4, 6, 8, 10, and 15 min, respectively.

From FIG. 4 it is evident that the final size distribution at a flow-rate of 5 ml/min is achieved within 6 minutes, which equals about 30 passes through the instrument (total instrument volume ~1 ml, 5 ml/min times 6 min equals 30 ml). Shearing times above 6 minutes increased the percentage of fragments within a range of 750–1500 base pairs only from approximately 91% to 93.5% as determined by densitometry, indicating that after a certain number of passages no further changes in the product can be discerned upon continued cycling. These results indicate that after the minimum size at a given velocity gradient has been obtained, the size distribution of sheared fragments does not change over time.

This final size distribution suggests that in a given shear gradient, only molecules above a certain size are cleaved while smaller ones escape fragmentation. Accordingly, if a cleaved molecule is still above a minimum size, it will be cleaved again on subsequent passages until it reaches a size small enough to escape fragmentation. In light of the above, the narrowest distributions will have a twofold spread in size if cleavage occurs in the middle of a molecule (see below): the highest molecular-weight material should have a little less than twice the molecular weight of the lowest molecular-weight material in the distribution.

These teachings are supported by results of experiments performed in support of the present invention, employing densitometry of agarose slab gels, PCR amplification and analysis of the cloned fragments, as well as by direct sequencing of the cloned fragments. The results corroborate that more than about 85% of all sheared fragments are consistently located within the aforementioned size distribution.

EXAMPLE 2

Effect of Ionic Strength on Shear Degradation

Figure 10:
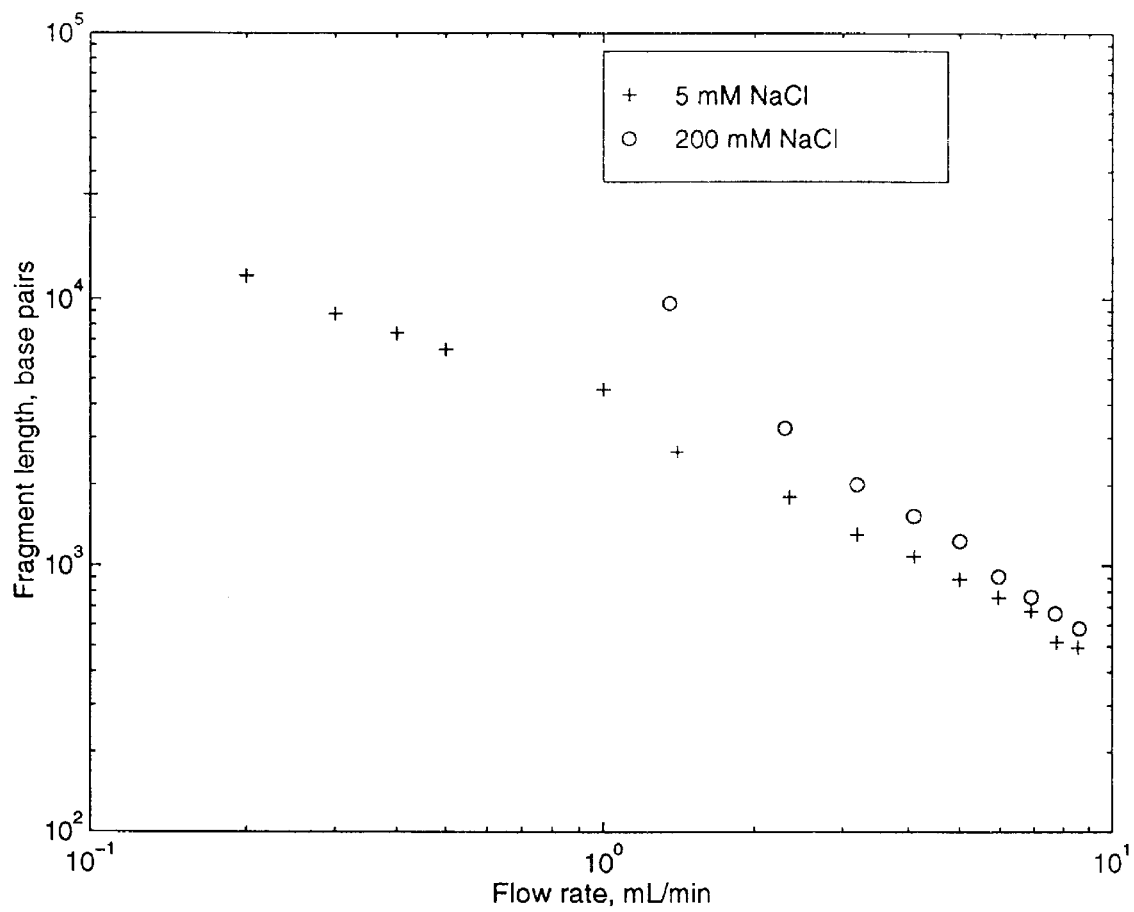
FIG. 10 shows the mean fragment length in base pairs plotted as a function of shear rate in 10 mM Tris-HCl, pH 7.6, and 0.1 mM EDTA, with either 5 mM NaCl or 200 mM NaCl.

FIG. 10 shows the mean fragment length in base pairs plotted as a function of shear rate in 10 mM Tris-HCl, pH 7.6, and 0.1 mM EDTA, with either 5 mM NaCl or 200 mM NaCl. The data show that an increase in ionic strength had a significant effect on the shearing process. A higher shear rate (based on the theoretical shear rate in an axis-symmetric point sink flow) was required to obtain identical breakage rates when shearing was carried out in 200 mM rather than 5 mM sodium chloride. These results are consistent with earlier studies of the effects of the ionic strength of a DNA solution on intrinsic velocity (Rosenberg and Studier, 1969), as well as on the relaxation time of T2 DNA (Adam and Zimm). All of these data indicate that DNA attains a progressively more coiled conformation at higher salt concentrations.

EXAMPLE 3

Mechanical Stress Reduces the Activation Energy Required for Bond Breaking

Figure 5:
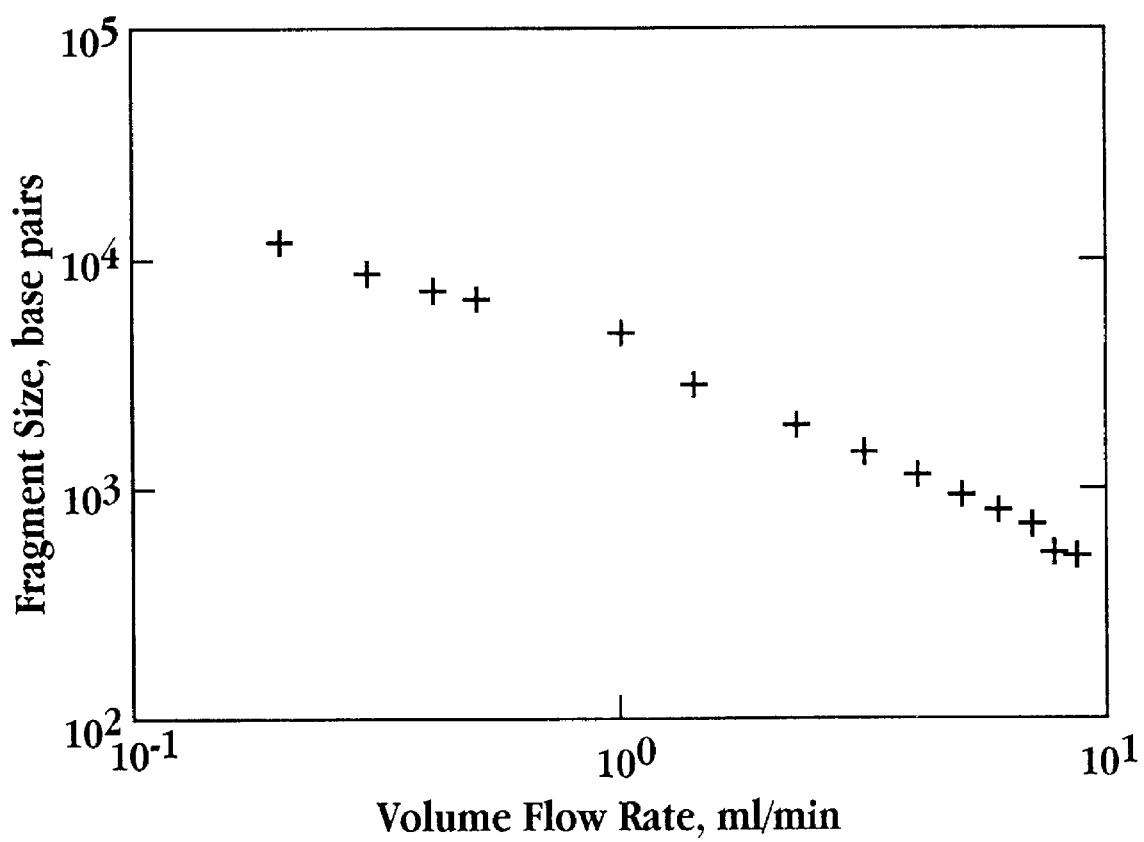
FIG. 5 shows the mean fragment length in base pairs plotted as a function of shear rate in 10 mM Tris-HCl, pH 7.6, 5 mM NaCl and 0.1 mM EDTA, assuming an effective capillary tube entrance of 28 $\mu$m.

FIG. 5 shows the mean fragment length in base pairs as a function of shear rate, assuming an effective capillary tube entrance of 28 $\mu$m. Only minimal degradation down to a size of approximately 5000 base pairs was obtained, when the 0.0025" I.D. tubing at the tee outlet was replaced with a 0.005" I.D. capillary tubing.

EXAMPLE 4

Other Parameters Affecting DNA Fragment Size Distributions

Figure 6:
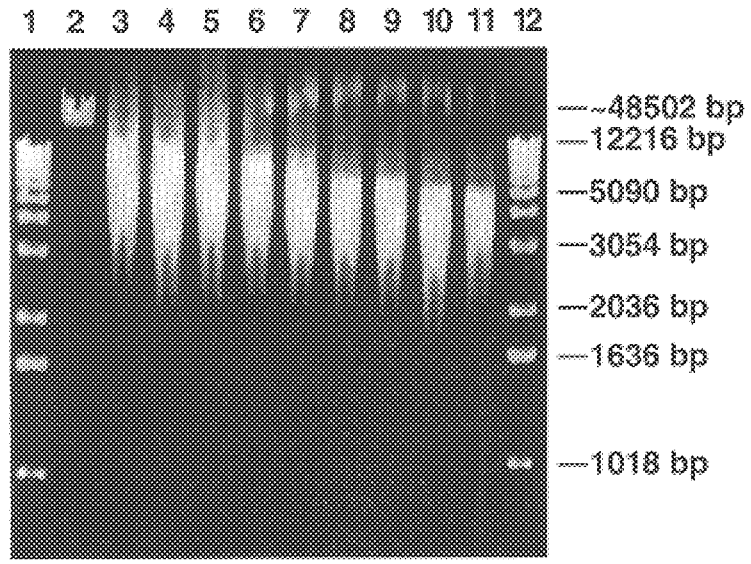
FIG. 6 shows an image of an agarose slab gel containing $\lambda$DNA sheared at various flow-rates using the apparatus shown in FIG. 1A equipped with the 0.62-$\mu$l stainless steel tee, but having the 0.0025" internal diameter (I.D.) PEEK tubing at its outlet having replaced with 0.005" I.D. stainless steel tubing.

FIG. 6 shows examples of λDNA sheared at various flow-rates by means of the apparatus depicted in FIG. 1A, which had been equipped with the 0.62-$\mu$l stainless steel tee, but with the 0.0025" I.D. PEEK tubing at its outlet having been replaced with a 0.005" I.D. stainless steel tubing. Lanes 1 and 12: 1 Kb DNA ladder (0.5 $\mu$g each); lane 2: unsheared λDNA (~0.1 $\mu$g); lanes 3–11: λDNA (4.08 $\mu$g) sheared at flow-rates of 1.4, 2.4, 3.25, 4.2, 5.15, 6.1, 7.05, 8.05, and 9.0 ml/min, respectively, for 8 min each.

Figure 7:
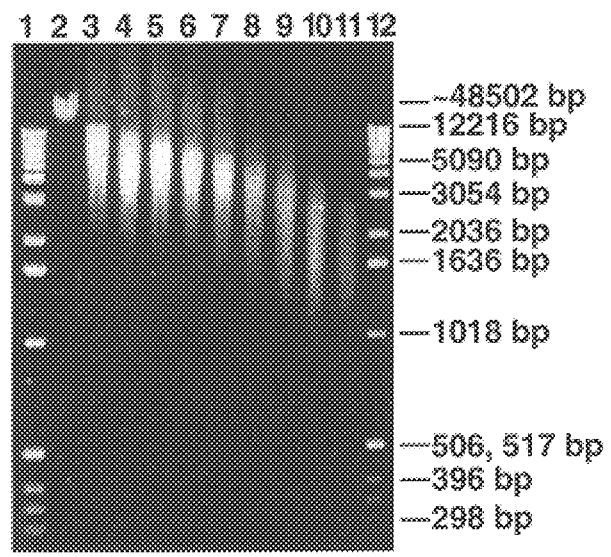
FIG. 7 shows an image of an agarose slab gel containing $\lambda$DNA sheared at various flow-rates using the apparatus shown in FIG. 1A equipped with the 0.62-$\mu$l stainless steel tee, but with the 0.0025" I.D. PEEK tubing relocated from the outlet of the tee to the outlet of the pressure transducer.

FIG. 7 shows examples of λDNA sheared at various flow-rates by means of the apparatus depicted in FIG. 1A, which had been equipped with the 0.62-$\mu$l stainless steel tee, but with the 0.0025" I.D. PEEK tubing having been relocated from the outlet of the tee to that of the pressure transducer. Lanes 1 and 12: 1 Kb DNA ladder (0.5 $\mu$g each); lane 2: unsheared λDNA (~0.1 $\mu$g); lanes 3–11: λDNA (4.08 $\mu$g) sheared at flow-rates of 1.4, 2.4, 3.25, 4.2, 5.15, 6.1, 7.05, 8.05, and 9.0 ml/min, respectively, for 8 min each.

Figure 8:
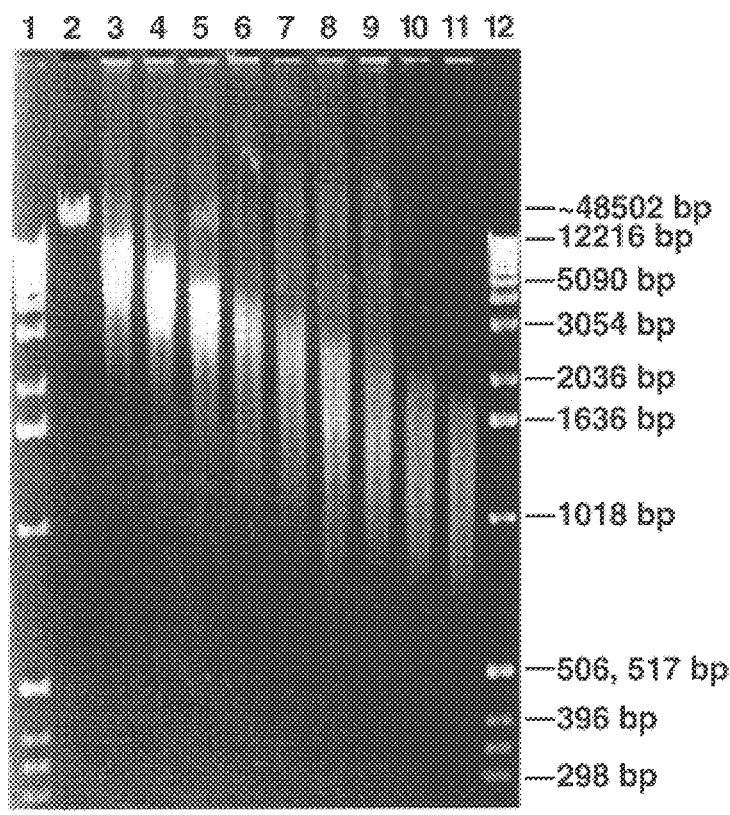
FIG. 8 shows an image of an agarose slab gel containing $\lambda$DNA sheared at various flow-rates using the apparatus shown in FIG. 1A equipped with a tee molded from PEEK.

FIG. 8 shows examples of λDNA sheared at various flow-rates by means of the apparatus depicted in FIG. 1A, which had been equipped with a tee molded from PEEK. Lanes 1 and 12: 1 Kb DNA ladder (0.5 $\mu$g each); lane 2: unsheared λDNA (~0.1 $\mu$g); lanes 3–11: λDNA (4.08 $\mu$g) sheared at flow-rates of 1.35, 2.3, 3.2, 4.1, 5.0, 5.95, 6.9, 7.7, and 8.6 ml/min, respectively, for 8 min each.

Figure 9:
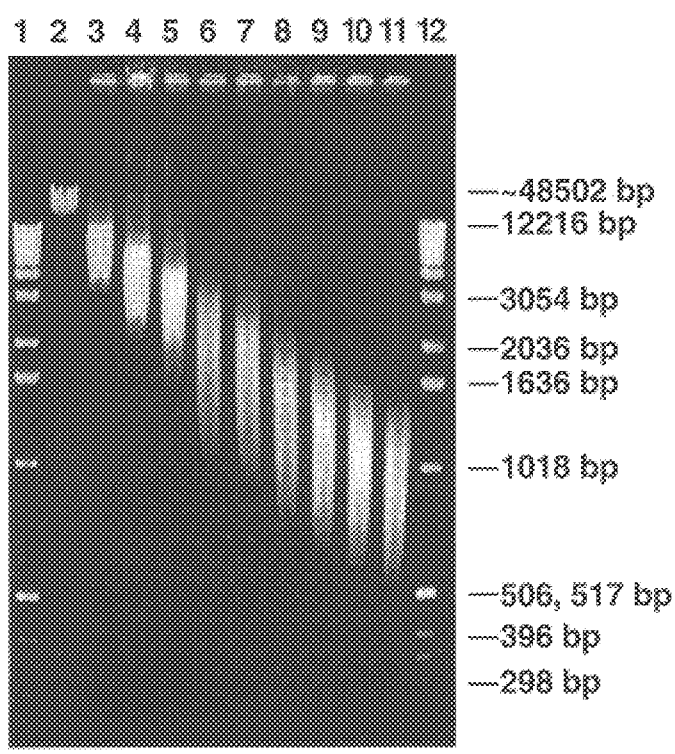
FIG. 9 shows an image of an agarose slab gel containing λDNA sheared at various flow-rates using the apparatus shown in FIG. 1A equipped with a static mixing tee molded from PEEK.

FIG. 9 shows examples of λDNA sheared at various flow-rates by means of the apparatus depicted in FIG. 1A, which had been equipped with a static mixing tee molded from PEEK. Lanes 1 and 12: 1 Kb DNA ladder (0.5 $\mu$g each); lane 2: unsheared λDNA (~0.1 $\mu$g); lanes 3–11: λDNA (4.08 $\mu$g) sheared at flow-rates of 1.35, 2.3, 3.2, 4.1, 5.0, 5.95, 6.9, 7.7, and 8.6 ml/min, respectively, for 8 min each.

Figure 11:
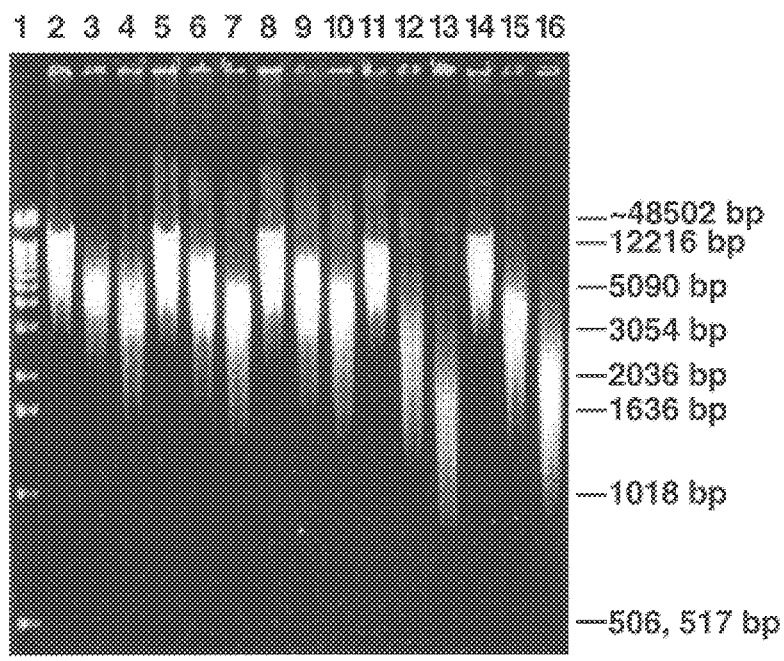
FIG. 11 shows an image of an agarose slab gel containing λDNA (2.04 μg) sheared in a single pass under various conditions at flow-rates of 2, 4.8, and 7.7 ml/min.

FIG. 11 shows examples of λDNA (2.04 $\mu$g) sheared in a single pass at flow-rates of 2, 4.8, and 7.7 ml/min, respectively, through either the 0.62-$\mu$l stainless steel tee (lanes 2–10) or the static mixing tee (lanes 11–16), with flow coming in through only one inlet (lanes 2–7, and 11–13), or simultaneously through both inlets (lanes 8–10, and 14–16), and a 4.8- (lanes 2–4, and 8–16) or 10-cm PEEK tubing of 0.0025" I.D. having been attached to the outlet. Lane 1: 1 Kb DNA ladder (0.5 $\mu$g).

Figure 12:
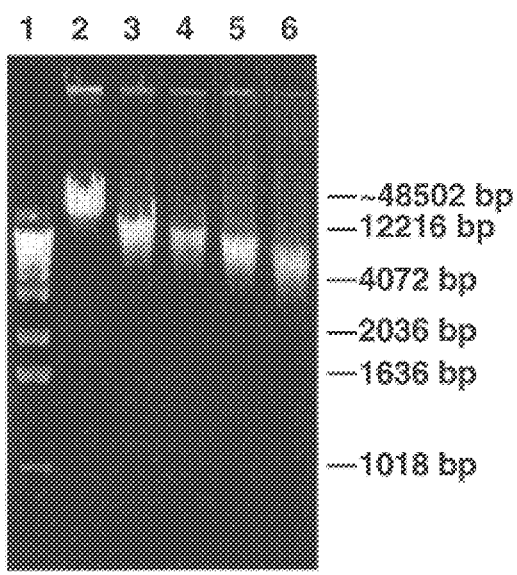
FIG. 12 shows the effect of the downstream location of the 0.0025" I.D. tubing on fragment size distribution.

FIG. 12 shows the effect of the downstream location of the 0.0025" I.D. tubing on fragment size distribution. Lane 1: 1 Kb DNA ladder (0.5 $\mu$g); lane 2: unsheared λDNA (~0.1 $\mu$g); lanes 3–6: λDNA (2.55 $\mu$g) sheared at flow-rates of 1, 2, 3, and 4 ml/min, respectively, for 8 min each, with a 50 cm×0.0025" I.D. tubing being attached to the outlet of the pressure transducer and a 10 cm×0.005" I.D. tubing having been placed between tee and inlet of pressure transducer. The pressure transducer is a coiled capillary, approximately 12 cm in length, having an inner diameter of about 0.04".

As shown above, moving the 0.0025" I.D. tubing farther downstream of the tee outlet resulted in significantly longer mean terminal fragment lengths at the same flow-rates. The only apparent change to the flow kinetics is the distance between the 90° flow bend in the tee and the region of high shear. These results support the teaching that an approximately 90° change in the direction of fluid flow, such as caused by a tee, serves to "condition" the flow (by establishing a component of extensional flow) so that the polymer (e.g., DNA) molecules are better aligned with the direction of maximum strain when they reach the contraction or orifice.

EXAMPLE 5

Evaluation of Cloning Efficiency

Cloning efficiency (CE) was determined by two methods. In the first, CE was quantitated as the ratio of tetracycline-sensitive (tet$^s$) to ampicillin-resistant (amp$^r$) transformants arising when DNA fragments were blunt-end ligated into the unique EcoRV site within the tet$^r$ gene of pBR322. In the second, the efficiency with which amp$^r$ transformants were obtained when increasing quantities of the DNA fragments were ligated to alkaline phosphatase-treated linearized pBR322 was employed a measure of CE.

Comparisons were made between the cloning efficiency of untreated HPLC-sheared λDNA fragments, those treated with Klenow (DNA fragments at 0.2 μM, in 50 mM Tris-HCl, pH 7.5, 10 mM MgCl$_2$, 1 mM DTT, 50 μg/ml BSA, and 25 μM each dNTP with 5 U Klenow (United States Biochemical, Cleveland, Ohio) in a 20 μl volume for 15 min at 30° C.), T4 DNA polymerase (DNA fragments at 0.2 μM, in 33 mM Tris-acetate, pH 7.9, 66 mM potassium acetate, 10 mM magnesium acetate, 0.5 mM DTT, 0.1 mg/ml BSA, and 25 μM each dNTP with 6 U T4 DNA polymerase (United States Biochemical) for 5 min at 37° C.), or T4 polynucleotide kinase (see below), and λDNA fragments obtained from HincII digestion (New England Biolabs, Beverly, Mass.).

λDNA fragments obtained from PstI and/or Eco47I digestion (New England Biolabs) with/without Klenow or T4 DNA polymerase treatment were concurrently cloned as controls for efficient end-repair. T4 polynucleotide kinase (5–10 U per 20 μl reaction volume; Life Technologies, New England Biolabs, or United States Biochemical) was utilized to treat HPLC-sheared λDNA fragments (for 30 min at 37° C.) under forward reaction conditions (0.2 μM DNA fragments, 50 mM Tris-HCl, pH 7.5, 10 mM MgCl$_2$, 5 mM DTT, 1.5 mM spermidine, 0.1 mM EDTA, and 0.1 mM ATP), exchange reaction conditions (0.2 μM DNA fragments, 50 mM imidazole-HCl, pH 6.4, 12 mM MgCl$_2$, 0.5 μM ATP, 0.3 mM ADP, and 15 mM β-mercaptoethanol), and optimal 3'-phosphatase conditions (0.2 μM DNA fragments, 0.1M MES, pH 6.5, 10 mM MgCl$_2$, 10 mM β-mercaptoethanol, and 50 μg/ml BSA); efficiency of incorporation under the first two conditions was monitored with γ$^{32}$P-ATP (NEN Dupont).

After EcoRV digestion (New England Biolabs), alkaline phosphatase-treated vector (10 μg linearized pBR322 in 400 μl 10 mM Tris-HCl, pH 8.0, incubated for 30 min at 37° C. with 0.04 U alkaline phosphatase (Boehringer Mannheim, Indianapolis, Ind.) was phenolchloroform extracted three times, chloroform extracted once, and ethanol precipitated. The concentrations of treated/untreated fragments and phosphatased/phosphorylated vector were determined immediately before use in ligation by spectrophotometry (estimating 50 μg/ml double stranded DNA for an OD$_{260}$ of 1).

Ligations were performed overnight at 16° C. in a 20 μl volume with 0.6 μg vector and an appropriate amount of fragment (0.82 μg when cloning into phosphorylated vector; 0–270 nM in incremental amounts when cloning into phosphatased vector), in 50 mM Tris-HCl, pH 7.8, 10 mM MgCl$_2$, 10 mM DTT, 1 mM ATP, and 50 μg/ml BSA, using 400 U T4 DNA ligase (New England Biolabs).

After heat inactivation (10 min at 70° C.), 3 μl of each ligation mix was transformed into Subcloning Efficiency DH5α competent cells (Life Technologies). Transformants were selected on Luria Broth (LB) plates containing 50 μg/ml ampicillin. Tetracycline-sensitive clones were screened by patching on LB plates containing 20 μg/ml tetracycline. Transformation of vector alone ligations was used to determine the background in these assays.

The fraction of clonable DNA fragments in a given sheared population (with and without additional end-repair) was estimated by determining the percent recombinants (tet$^s$/amp$^r$ transformants) relative to the percent recombinants obtained for HincII-digested λDNA. HincII digestion was chosen because it produces 35 blunt-ended fragments per λDNA ranging in size from 228 bp to 4755 bp. Sheared fragments, averaging about 1000 bp in length, resulted in approximately 50 fragments per λDNA.

Alternatively, the number of transformants obtained per μg vector was plotted against nM fragment ends (estimated for sheared fragments by assuming 50 fragments per λDNA). The fraction of clonable fragments in comparison to HincII-digested λDNA was then determined as the ratio of slopes at the linear portion of the curves.

Both methods demonstrated that approximately 20–40% of λDNA fragments sheared using the methods and apparatus of the present invention can be cloned in the absence of additional end-repair. No consistent improvement in cloning efficiency was observed by treatment with Klenow, T4 DNA polymerase, or T4 polynucleotide kinase, indicating that DNA fragments sheared using the methods and apparatus of the present invention may be cloned without additional enzymatic treatment.

EXAMPLE 6

Determination of the DNA Sequence Adjacent to the Cleavage Site

To determine the sequence of the fragment ends, 0.4–5 μg of cosmid or P1 cloned human DNA was sheared using the apparatus described with respect to FIG. 1A in 10 mM Tris-HCl, pH8.0, 5 mM NaCl, and 1 mM EDTA. After 8 minutes, 1 ml of sheared fragments was collected into a "CENTRICON 30" (Amicon, Beverly, Mass.) concentrator. The samples were concentrated to 50 μl by centrifugal dialysis according to the manufacturers instructions. One ml of TE (10 mM TRIS, 1 mM EDTA) was added to each centricon and the centrifugal concentration repeated. Vector DNA was prepared by digestion of M13mp19 (New England Biolabs) with SmaI (New England Biolabs) and treatment with Calf Intestinal Alkaline Phosphatase according to the manufacturers instructions (Boehringer-Mannheim, Mannheim, Indianapolis, Ind.).

In some cases the sample was cloned directly; in others, the sheared DNA was first gel purified and isolated using a Geneclean II kit (Bio101, La Jolla, Calif.) according to the manufacturers instructions. Ligations were carried out in 20 μl with 20 ng of vector and 10–100 ng of sheared DNA. The ligations were incubated for 10–16 hours at 16° C. with T4 DNA ligase (New England Biolabs) in 50 mM Tris-HCl, pH 7.8, 10 mM MgCl$_2$, 10 mM DTT, 500 μM ATP, 25 μg/ml BSA, at 65° C. for 5 minutes, electroporated into DH10B cells and then plated on DH5alpha F' plating cells (both were obtained from Gibco BRL LifeTechnologies) prepared according to Maniatis, et al. (1982).

A total of 1000–40,000 recombinant clones were produced in each library. Without gel purification the libraries contained 5–10% of short inserts (less than 400 base pairs, in some cases as short as 80 base pairs). From each cosmid or P1 clone, between 1000 to 3000 clones were sequenced using the dye-primer sequencing chemistry from the Applied Biosystems Division of Perkin-Elmer (Foster City, Calif.).

Results of the experiments described above suggest that most fragments were cleaved at random with respect to the sequence at the cleavage site. DNA fragments sheared using the methods of the present invention were cloned directly (without any enzymatic treatment) into a SmaI cut, phosphatased vector as described in the Materials and Methods, above. All 64 of the potential triplets that might be found at a cleavage site were found in a set of 288 sites either on the cloned or the uncloned side of the break. The two most abundantly represented triplets were CTT (28 times) and TTT (27 times).

Breakage seemed to occur slightly more frequently at sites having at least two AT-base pairs on either side of the cleavage site (24 times) compared to breakage points having at least two GC-base pairs (12 times). Overall, however, these so-called AT-rich regions represented only 8.3% of all cleavage sites. Moreover, in the adjoining triplets the GC content was 45%, reflecting the overall GC content of the DNA sequences subjected to hydrodynamic shear breakage.

EXAMPLE 7

Determination of Fragment Distribution in a Cosmid

For cosmid subfragment cloning, adaptors with a CAAAC overhang were either ligated directly to the sheared DNA fragments overnight at 16° C. with T4 DNA ligase, or after end-repair of the DNA fragments with T4 DNA polymerase at 11° C. for 60 minutes. Following ligation, the cosmid subfragments were separated from adaptor dimers by means of slab gel electrophoresis on a low-melting 0.8% agarose gel. Subsequently, they were ligated into M13 vector at 16° C. overnight with T4 DNA ligase and transformed into NM 522 *E. coli* cells (Promega, Madison, Wis.).

Subclone DNAs were prepared by lysis of the phages in ethanol/butanol (5:2, volume/volume [v/v]), purification of the released DNA with Cleanascite (Affinity Technologies, New Brunswick, N.J.), followed by ethanol precipitation. Subclones were sequenced on a Catalyst 800 Cycle Sequencer (Perkin-Elmer, Applied Biosystems Division, Foster City, Calif.) using a linear amplification method with fluorescent dye-primers, followed by electrophoresis on a 4.75% acrylamide gel run on an Applied Biosystems Model 373 Stretch Sequencer.

These results demonstrated that a substantial number of fragments could be ligated and cloned into a M13 vector without prior end-repair with T4 polymerase. This is again in contrast to results reported for fragments generated by sonic degradation, which are reportedly difficult if not impossible to clone without end-repair (Deininger, et al., 1983).

While the invention has been described with reference to specific methods and embodiments, it is appreciated that various modifications and changes may be made without departing from the invention.

It is claimed:

1. An apparatus suitable for producing a defined size distribution of polynucleotide fragments in a polynucleotide suspension, said apparatus comprising:
    (i) a shearing assembly, said assembly comprising:
        (a) a capillary,
        (b) an orifice plate disposed within said capillary, said plate having an orifice with a diameter greater than about 0.001" and less than about 0.003", and
        (c) a port for injection of a polynucleotide suspension;
    (ii) a pumping means effective to pass said polynucleotide suspension through said shearing assembly at a flow rate of at least about 1 ml/minute in a manner that does not generate air bubbles within the fluid suspension; and
    (iii) a repeat pass means effective to pass said polynucleotide suspension through said shearing assembly a plurality of times, wherein said defined size distribution of polynucleotide fragments has a size range with a selected mean between about 100 and 20,000 bp, and where the largest polynucleotide fragment in the size distribution is about twice as large as the smallest polynucleotide fragment in the size distribution.

2. The apparatus of claim 1, wherein said orifice has a diameter of between about 0.002" and about 0.003".

3. The apparatus of claim 2, wherein said orifice has a diameter of about 0.0025".

4. The apparatus of claim 1, wherein said repeat pass means is effective to recirculate the polynucleotide suspension through the shearing assembly via unidirectional flow through a closed loop.

5. The apparatus of claim 1, wherein said repeat pass means uses a reciprocating motion, where the polynucleotide suspension is passed back and forth through the shearing assembly by alternating the direction of flow of the suspension.

6. The apparatus of claim 1, wherein said pumping means is effective to pass said polynucleotide suspension through said shearing assembly at a flow rate of between about 3.0 ml/minute and about 12 ml/minute.

7. The apparatus of claim 1, wherein said pumping means is an HPLC pump.

8. The apparatus of claim 1, wherein said pumping means is a syringe pump.

9. The apparatus of claim 1, wherein said shearing assembly further includes a means for inducing extensional flow of said suspension in said capillary upstream of said orifice.

10. The apparatus of claim 9, wherein said means for inducing extensional flow is a tee.

11. The apparatus of claim 10, wherein said tee has an internal volume of between about 0.5 $\mu$l and about 5 $\mu$l.

12. The apparatus of claim 10, wherein said tee is positioned between about 1 mm and about 5 mm upstream of said orifice.

13. The apparatus of claim 1, further comprising an automated control means for controlling steps during operation of the apparatus.

14. The apparatus of claim 13, wherein said control means comprises a computer.

15. A method of producing a defined size distribution of sheared polynucleotide fragments having a size range with a selected mean between about 100 and 20,000 bp, and where the largest polynucleotide fragment in said size range is about twice as large as the smallest polynucleotide fragment in said size range, comprising:
    (i) passing a polynucleotide suspension through a shearing assembly at a flow rate of between 1 ml/min and 23 ml/min, said shearing assembly comprising:
        (a) a capillary,
        (b) an orifice plate disposed within said capillary, said plate having an orifice with a diameter of less than 0.005", and
        (c) a port for injection of said polynucleotide suspension,
    wherein said passing results in shearing polynucleotides in the suspension into sheared polynucleotide fragments; and
    (ii) repeating step (i) until said sheared polynucleotide fragments have selected mean between about 100 and 20,000 bp, and the largest polynucleotide fragment in said size range is about twice as large as the smallest polynucleotide fragment in said size range.

16. The method of claim 15, wherein said orifice has a diameter of between about 0.002" and about 0.003".

17. The method of claim 16, wherein said orifice has a diameter of about 0.0025".

18. The method of claim 15, wherein said suspension of polynucleotide fragments is passed through said shearing assembly at a flow rate of between about 3.0 ml/minute and about 12 ml/minute.

19. The method of claim 15, wherein said polynucleotide fragments are DNA fragments.

20. The method of claim 15, wherein said DNA fragments are genomic DNA fragments.

21. The method of claim 15, wherein said DNA fragments are double-stranded DNA fragments.

22. The method of claim 15, wherein said DNA fragments are single-stranded DNA fragments.

23. The method of claim 15, wherein step (i) is repeated between about 10 and about 50 times.

24. The method of claim 23, wherein step (i) is repeated between about 15 and about 30 times.

25. The method of claim 15, wherein said selected mean is between about 200 and about 10,000 basepairs.

26. The method of claim 15, wherein said selected mean is between about 400 and about 4,000 basepairs.

* * * * *